US006376229B2

(12) United States Patent
Morris et al.

(10) Patent No.: US 6,376,229 B2
(45) Date of Patent: *Apr. 23, 2002

(54) METHOD FOR PRESERVATION OF MARINE MICROORGANISMS

(75) Inventors: Barrington A. Morris, Coral Springs, FL (US); Eric A. Goulbourne, Jr., Hamilton, OH (US)

(73) Assignee: World Wide Imports Enterprises, Inc., Ft. Lauderdale, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/438,672

(22) Filed: Nov. 12, 1999

Related U.S. Application Data

(60) Provisional application No. 60/117,959, filed on Jan. 29, 1999.

(51) Int. Cl.[7] .............................. C12N 1/04; C12N 1/20; C12M 1/00
(52) U.S. Cl. .................. 435/260; 435/307.1; 435/253.6
(58) Field of Search .............................. 435/260, 307.1, 435/253.6

(56) References Cited

U.S. PATENT DOCUMENTS

| 4,874,707 A | 10/1989 | Bock ........................ 435/253.6 |
| 4,999,301 A | 3/1991 | Bryan-Jones ............ 435/252.5 |
| 5,314,542 A | 5/1994 | Cassidy ....................... 119/231 |
| 5,733,774 A | 3/1998 | Jin ............................. 435/260 |

OTHER PUBLICATIONS

Kerry et al. Aquaculture. 1996. vol. 144, pp. 103–119.*
Atlas R. Handbook of Microbiological Media. CRS Press. 1993. pp. 201 ,237,544,545,563,861.*

* cited by examiner

*Primary Examiner*—Sandra E. Saucier
*Assistant Examiner*—Vera Afremova
(74) *Attorney, Agent, or Firm*—Stearns Weaver Miller Weissler Alhadeff & Sitterson, P.A.

(57) ABSTRACT

A method of harvesting and packaging marine substrate material with an optimal amount of water and air in retail packaging specifically dimensioned and configured for maintaining ammonia oxidizing bacteria in a state wherein the bacteria are capable of metabolic and physiologic activity after prolonged periods at room temperature. According to a first aspect of the invention there is disclosed a method for the harvesting materials that are naturally rich with bacteria, such as sand, shells, aragonite, and crushed coral materials harvested from submerged marine environments, and packaging the harvested materials in specifically sized sealed containers, suitable for storage at room temperature and retail sale, such that marine bacteria are preserved in their natural habitat—in biofilms attached to the granular surfaces—for extended periods of time. According to a second aspect of the invention there is disclosed an enrichment solution for further extending the period of time that the microorganisms remain bio-actively viable. The enrichment solution may be used in combination with the method of the first aspect of the invention to further increase the number of microorganisms that remain bio-actively viable.

5 Claims, 3 Drawing Sheets

Figure 1

Sea Water Enrichment Solution

To 940 mL of sea water add:

| Quantity | Compound | Stock Solution |
|---|---|---|
| 1.0 mL | $NaNO_3$ | 75.0 g/L of distilled water |
| 1.0 mL | $NaH_2PO_4 \cdot H_2O$ | 5.0 g/L of distilled water |
| 1.0 mL | Trace Metal Solution | (see Figure 2) |
| 0.5 mL | Vitamin Solution | (see Figure 3) |
| 50 mL | Organics Stock Solution | (see Figure 4) |

Make final volume up to 1.0 L with sea water. Filter sterilize after all additions.

Figure 2

Trace Metal Solution

To 950 mL of distilled water add:

| Quantity | Compound | Stock Solution |
|---|---|---|
| 3.15 g | $FeCl_3 \cdot 6H_2O$ | - |
| 4.36 g | $Na_2EDTA \cdot 2H_2O$ | - |
| 1.0 mL | $SrCl_2 \cdot 6H_2O$ | 9.8 g/L distilled water |
| 1.0 mL | $K_2MoO_4 \cdot 2H_2O$ | 6.3 g/L distilled water |
| 1.0 mL | $ZnSO_4 \cdot 7H_2O$ | 22.0 g/L distilled water |
| 1.0 mL | $CoCl_2 \cdot 6H_2O$ | 10.0 g/L distilled water |
| 1.0 mL | $MnCl_2 \cdot 4H_2O$ | 180.0 g/L distilled water |

Make final volume up to 1.0 L with distilled water. Filter sterilize.

Figure 3

Vitamin Solution

To 950 mL distilled water add:

| Quantity | Compound | Stock Solution |
|---|---|---|
| 1.0 mL | Vitamin B12 (Cyanocobalamin) | 1.0 g/L of distilled water |
| 10.0 mL | Biotin | 0.1 g/L of distilled water |
| 200.0 mg | Thiamine HCl | - |

Make final volume up to 1.0 L with distilled water. Filter sterilize into plastic vials and store in refrigerator.

Figure 4

Organics Stock Solution

To 900 mL of distilled water add:

| Quantity | Compound |
|---|---|
| 1.0 g | Sodium Acetate |
| 6.0 g | Glucose |
| 3.0 g | Sodium Succinate |
| 4.0 g | Peptone |
| 2.0 g | Yeast extract |

Bring up to 1.0 L with distilled water. Filter sterilize and dispense into 50 mL aliquots.

| Approximate Date Tested | Log CFU/Pound of Aragonite (with Enrichment Solution) |
|---|---|
| Initial | 7.62 |
| 3 months | 7.57 |
| 6 months | 7.70 |
| 9 months | 7.38 |
| 12 months | 7.32 |

METHOD FOR PRESERVATION OF MARINE MICROORGANISMS

CROSS-REFERENCE TO RELATED APPLICATIONS

This application claims the benefit of U.S. Provisional Patent Application Serial No. 60/117,959, filed Jan. 29, 1999.

STATEMENT REGARDING FEDERALLY SPONSORED RESEARCH OR DEVELOPMENT

Not Applicable

BACKGROUND OF THE INVENTION

1. Field of the Invention

The present invention relates to a the preservation of microorganisms, and, more particularly to a method for preserving oceanic microorganisms in an aqueous solution within sealed packaging providing conditions favorable for survival for periods in excess of twelve (12) months. One aspect of the invention relates to a method for packaging marine substrate material, such as sand, aragonite, coral rock and crushed coral in an aqueous solution contained within packaging, suitable for retail display and sale, wherein a suitable environment is present so that marine microorganisms remain in biofilms attached to the surface of the material for extended periods of time. A further aspect of the invention relates to the discovery of a nutrient rich seawater enrichment solution containing vitamins, organics stock, trace metals, and $NaNO_3$ and $NaH_2PO_4H_2O$ for further extending the period of time wherein the organisms remain bio-active.

The invention provides for the effective harvesting, packaging, transport, bio-active storage, and retail sale of aquarium substrate material containing live microorganisms, such as bacteria useful in oxidizing ammonia in aquariums, whereby the microorganisms remain biologically viable for extended periods of time in excess of twelve (12) months thereby maintaining a stable and healthy aquarium environment.

2. Description of Related Art

Aquariums have experienced a boom in popularity in recent years. Many saltwater aquariums include a diverse mix of tropical fish, live coral formations, and other exotic marine life. Saltwater marine organisms are directly affected by the chemical, biological, and physical characteristics of their environment. A number of environmental factors are critical to maintaining the delicate balance required for a healthy aquarium environment. Factors such as water temperature, pH level, lighting conditions, and complex chemical balances must constantly be maintained and monitored. The introduction of fish and other marine animals into an aquarium causes a series of chemical changes often resulting in chemical imbalances that are not conducive to aquatic life. It is therfor crucial to maintain a high level of water quality.

The initial set up of a marine aquarium typically requires a conditioning period that can take up to six (6) weeks depending upon the aquarium conditions and temperature. During the conditioning period the chemical composition of the water undergoes a series of changes and waste products can quickly build-up to levels that are toxic to aquarium life. The introduction of fish, plants, and food into an aquarium begins a natural process often referred to a "biochemical cycling".

A significant change in the chemical composition of the water involves the accumulation of ammonia The process begins when fish and invertebrates excrete waste. The excreted waste increases the amount of ammonia present in the water as a result of decaying food and organic compounds. Harmful ammonia and nitrite are constantly converted into less harmful nitrates, which in turn is used by plants and algae for food. Aquariums are full of both autotrophic and heterotrophic bacteria that attach, grow, and form biofilms where the bacteria convert toxic nitrogeneous compounds and ammonia into harmless products. Nitrobacter and Nitrosomonas are examples of autotrophic bacteria that use oxygen to oxidize ammonia ($NH_4$) to nitrite ($NO_2$) and Nitrate ($NO_3$).

Ammonia is a toxic waste product which, if unchecked, can accumulate and cause injury or death to aquarium inhabitants. In fact, the presence of ammonia in aquarium water is the number one cause of death in aquarium fish. The primary sources of ammonia are decaying organic material (such as uneaten food) and waste excreted by fish, other animals and organisms. An ammonia level as low as 0.5 parts-per-million (PM) creates stress in fish and compromises the natural immune systems of fish and other aquarium inhabitants. An ammonia level of 2 PPM has been found to cause the natural immune system of the fish and other aquarium inhabitants to fail or otherwise cease fuctioning. Accordingly, maintaining ammonia levels is critical to the health of the aquarium habitat.

The accumulation of ammonia is often caused by the lack of sufficient numbers of Nitrosomonas. Nitrosomonas is a genus of bacteria in aquaria that oxidize ammonia thereby regulating the ammonia level. Nitrosomonas, and other ammonia oxidizing bacteria, are found in natural abundance in marine materials, such as sand, aragonite, and crushed coral, harvested from the ocean floor. Nature provides many types of bacteria that, in the presence of oxygen, carry out the oxidation of ammonia to nitrites and eventually to nitrates in a process known as nitrification. It has been found that such bacteria settle on marine materials, such as aragonite (reef sand), and eventually form a biofilm. Marine nitrifying bacteria in the biofilm oxidize ammonia to nitrite, and nitrite to nitrate. Accordingly, these natural marine materials provide a natural source of ammonia oxidizing bacteria for use in maintaining ammonia levels in aquarium environments. Nitrate not utilized by plants is removed by other bacteria in the absence of oxygen (the anaerobic environment found in the lower levels of the sediment) in a process called denitrification.

While marine nitrifying bacteria are found in abundance in natural materials, such as aragonite harvested from the ocean floor, it has been found that there are generally three conditions that are required to maintain the nitrification process. These conditions are: (1) a surface upon which bacteria can attach, grow, and from a biofilm; (2) ammonia to start the process; and (3) an aerobic environment. The absence of any of the above-referenced conditions will either prevent of delay the nitrification process.

The initial set-up of aquariums presents unique biochemical circumstances that must be addressed in order to produce and maintain a healthy environment for marine life. The initial cycling of organic compounds in an aquarium started with dry sand or gravel often takes a period of several weeks during which an ammonia source (often only one or two small fish) provides an environment wherein beneficial bacteria to establish and begin to flourish eventually forming a biofilm. It has been found that the long initial cycling period realized when starting an aquarium with dry sand or gravel results from the time required for bacteria to attach, grow and form a biofilm on the previously dry, and organically inactive, sand and gravel. It has been shown that the initial cycling period can be substantially reduced by the introduction of bacteria rich "wet" sand and gravel that has been recently harvested from the ocean and thus contains an abundance of bacterial biofilm. Marine sand and gravel harvested from the ocean or riverbeds contain both autotrophic and heterotropic bacteria in their natural state (i.e. established biofilms on the sand particles), each of which facilitate the rapid cycling of an aquarium. Accordingly, there exists a need for a method of harvesting and packaging marine materials such as aragonite reef sand, gravel, crushed coral and the like, such that the bacteria remain metabolically and physiologically active for extended periods of time in excess of twelve (12) months in retail packaging at room temperature.

It has proven difficult, however, to maintain ammonia oxidizing bacteria and other useful bacteria in a biologically active state during the extended period beginning with the harvesting of the material and ending with the purchase by a consumer and delivery into an aquarium; a time period often reaching up to six (6) months or more. The difficulty is increased where the harvested materials must be stored for extended periods in retail packaging at room temperatures.

The background art reveals several references directed to preserving bacteria and the like, but none of the references adequately address the problems encountered in maintaining ammonia oxidizing bacteria bio-actively viable bio-film for extended periods.

U.S. Pat. No. 4,874,707, issued to Bock, discloses a complex laboratory process for producing an aqueous suspension of nitrifying bacteria using a growth medium containing ammonia or nitrite, in which the bacteria remain metabolically and physiologically active even after a storage period of one year or more at 30° C (i.e. approximately room temperature). According to Bock, air, pure oxygen, or a mixture of air and pure oxygen is passed through a gas permeable non-porous tube submerged in a suitable culture medium. As a result of positive aerotaxis, nitrifying bacteria adhere on the tube surface, forming a biofilm of extracellular polymers. The bacteria are grown in the dark at a constant temperature of 30° C. When a stationary growth phase has been reached the oxygen supply is stopped.

U.S. Pat. No. 4,999,301, issued to Bryan-Jones, a method whereby microorganisms are stored for long periods of time in storage mediums containing a high concentration of nutrients and growth inhibiting substances to maintain the microorganisms, such as bacteria, in the stationary phase of their growth cycle. The concentrated medium disclosed by Bryan-Jones contains an excess of essential nutrients while the microorganisms are in the "death phase." When the concentrated medium is diluted to below the concentration that inhibits microorganism growth, the microorganisms will start to increase in number and grow. The claims of the Bryan-Jones reference are united to bacteria selected from the group comprising Lactobacillus plantarum and Bacillus subtilus. E.g. claim 1. In addition, the '301 patent claims a bacterial culture kit having bacteria in a growth medium comprising from 10% to about 30% solids which function to delay the onset of the normal "death phase". The solids are disclosed as waste products from a food manufacturing process or an alcohol fermentation process. See, e.g. Column 2, lines 46–58. Bryan-Jones discloses a storage medium consisting of wheat spent wash syrup and acetate/acetic acid buffer and sucrose. Bryan-Jones claims that an advantage of such a kit is that a sufficient number of the microorganisms will remain viable when the kit is sold to a consumer such that the microorganisms will start to increase in number and grow after purchase.

U.S. Pat. No. 5,314,542, issued to Cassidy et al., discloses a culture of Nitrosomonas packaged in a manner to induce a metabolic state of dormancy under conditions favorable for survival of up to at least one year at room temperature. Upon obtaining culturing media with the maximum obtainable cell concentration, the media is concentrated to approximately one twenty-fifth (1/25) of its volume by centrifugation or filtration. See Col. 3, lines 5–9. The concentrate is resuspended in sterile water of "suitable salinity" and packaged in sterile opaque containers wherein Cassidy et al. claim that the cells will remain viable for at least one year. According to Cassidy et al., the majority of the resuspended cells packaged in this manner enter a metabolic state of inactivity (i.e. dormancy). The disclosure further states that the preserved cells can at any time be returned to their metabolically active state by adding ammonium chloride (or other suitable salt) to the opaque container to bring the ammonia concentration to about 200 ppm. There is also disclosed a method for rapid reactivation to complete metabolic activity within about 72 hours and subsequent addition into aquaria to begin oxidation and prevention of harmful ammonia accumulation in aquaria.

U.S. Pat. No. 5,733,774, issued to Jin et al., discloses stabilized bacteria which can survive long term storage at high temperatures. According to the method disclosed by Jin et al., bacteria are dried until they reach a dormant state. Suitable methods include air drying, vacuum drying etc. See, Col. 2, lines 1–3. Next Oxygen is then removed from the environment surrounding the bacteria to prevent oxidative damage to the dormant cells. The bacteria is then packaged and stored in material impermeable to gas and water vapor, whereby Jin claims the bacteria will remain stable and efficacious for at least a year.

The methods disclosed by the background art have proven too complex and inadequate for widespread acceptance and use in the aquarium industry. Accordingly, there exists a need for a method for obtaining and preserving ammonia oxidizing bacteria for retail sale and use in connection with saltwater aquaria.

BRIEF SUMMARY OF THE INVENTION

It is an object of the present invention to provide a method for preserving saltwater marine organisms for extended periods of time such that the organisms remain capable of metabolic and physiologic activity.

Another object of the present invention is to provide a method for harvesting and packaging marine substrate material with an optimal amount of seawater and air in packaging specifically configured for maintaining ammonia oxidizing bacteria in a state wherein the bacteria are capable of metabolic and physiologic activity after a prolonged period, at room temperature.

Still another object of the present invention is to provide an enrichment solution for prolonging the bio-active shelf life of marine microorganisms present in packaged marine substrate materials, such as aragonite, crushed coral, and sand.

Yet another object of the present invention is to provide a method for harvesting and packaging bio-actively optimal quantities of marine substrate material, air, seawater, and an enrichment solution for maintaining marine organisms in a biologically viable state for extended periods of time.

Still another object of the present invention is to provide packaging material that is specifically sized for prolonging the bio-active state of marine organisms when packaged in certain optimal quantities.

Yet another object of the present invention is to provide a method and composition for the preservation of microorganisms, associated with sand, shells, and coral materials harvested from natural marine environments, whereby the materials may be packaged in sealed containers, suitable for retail sale, within a unique enriched seawater solution.

In accordance with these and other objects which will become apparent hereinafter, the instant invention will now be described with particular reference to the accompanying drawings.

BRIEF DESCRIPTION OF THE SEVERAL VIEWS OF THE DRAWINGS

FIG. 1 shows a formula for a seawater enrichment solution according to the present invention;

FIG. 2 shows the formula for the trace metal solution referenced in FIG. 1;

FIG. 3 shows the formula for the vitamin solution referenced in FIG. 1;

FIG. 4 shows the formula for the organics stock solution referenced in FIG. 1;

DETAILED DESCRIPTION OF THE INVENTION

Figure 5:
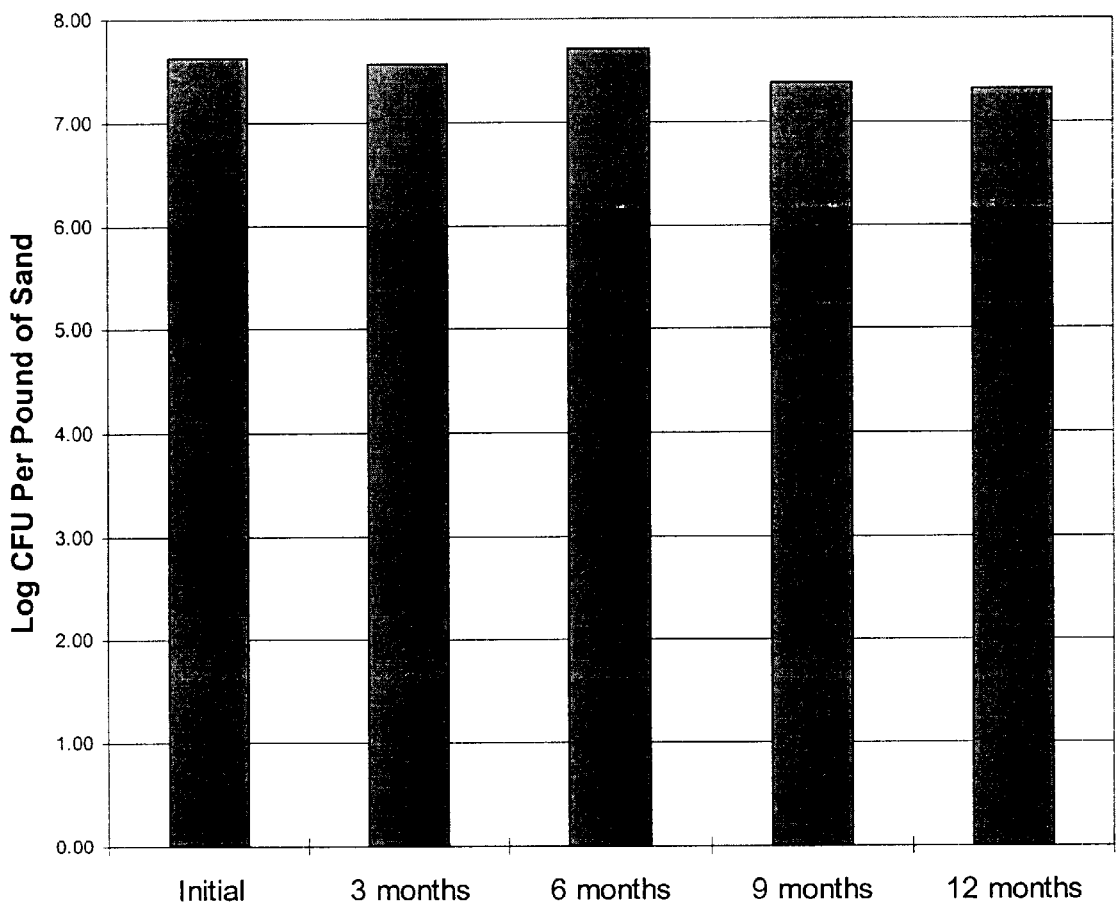
FIG. 5 is a graph depicting the number of colony forming units per pound ("CFU/Pound") of aragonite sand measured along the Y-axis and time in months measured along the X-axis as found on average in two different bags of aragonite packaged with an enrichment solution according to the present invention.

According to a first aspect of the present invention there is disclosed a method for preserving saltwater marine microorganisms, harvested from a natural marine environment, in retail packaging for subsequent introduction into an aquarium environment to facilitate rapid biochemical cycling. As used herein the term "marine microorganisms" and/or "microorganisms" shall mean aquatic bacteria naturally found in saltwater environments. Specifically, the method provides for the harvesting materials that are naturally rich with bacteria, such as sand, shells, aragonite, crushed coral materials, river rocks and pebbles and the like, harvested from submerged marine and/or river environments, and packaging the harvested materials in specifically sized sealed containers, suitable for storage at room temperature and retail sale, such that marine bacteria are preserved in their natural habitat—in biofilms attached to the granular surfaces—for extended periods of time. The method provides the aquarium industry with a useful means for prolonged storage of marine materials while maintaining microorganism bio-activity (i.e. metabolic and physiologic activity) such that, upon introduction into an aquarium environment the microorganisms are effective in biochemical cycling of the aquarium environment and stabilizing ammonia levels thereby resulting in an aquarium environment which is optimal for fish and other living organisms. According to a second aspect of the present invention there is disclosed an enrichment solution for further extending the period of time that the microorganisms remain bio-actively viable. The enrichment solution may be used in combination with the method of the first aspect of the invention to further enhance the period of time that microorganisms remain bio-actively viable.

A first aspect of the present invention includes packaging marine substrate materials, such as aragonite, sand, crushed coral and the like according to the following steps:
1. Harvesting marine substrate material from a submerged marine environment;
2. Packaging the harvested marine material in said packaging along with saltwater and air in the following relative ratios: 1 lb. of sand with 2–12 fluid oz. (preferably between 4–6 fluid oz.) water and 5–100 $cm^3$ (preferably between 10–50 $cm^3$) of air.
3. Sealing the packages in an airtight manner.

It has been found that bacteria associated with marine material harvested and packaged in accordance with the above-referenced method steps is metabolically and physiologically active upon introduction into all aquarium environment. The process thus provides an optimal saltwater preservation solution and packaging method that results in the preservation of autotrophic marine bacteria in their natural habitat, i.e. a biofilm existing on the surfaces of the granular material. It is significant to the rapid cycling of aquarium tanks that the bacteria exist in biofilms as the bacterial in such a state are instantly capable of cycling harmful metabolic end products upon introduction into the aquarium environment.

In contrast, the introduction of bacteria that has been cultured according to teachings of the background art, or bacteria that otherwise exists in a non-biofilm state, requires a substantial number of days and/or weeks to attach to aquarium materials and form biofilms prior to contributing to aquarium cycling.

Marine materials packaged according to the methods of the present invention are capable, upon introduction into an aquarium environment, of carrying out rapid biochemical cycling essential to the maintenance of a successful aquarium. Each pound of granular material harvested and packaged according to the present invention contains in excess of 10 million live bacteria. Each of the above-referenced steps contributes to a method of packaging harvested marine material whereby both autotrophic and heterotrophic bacteria survive in sealed packaging for longer periods of time than if packaged without one or more of the steps.

The first step provides for harvesting marine substrate material from a submerged marine environment and initially storing the harvested marine material in a sealed container with seawater. Harvesting the marine material from a submerged marine environment, as opposed harvesting dry material such as sand and crushed coral, is critical in obtaining material having an abundance of autotrophic and heterotrophic bacteria flourishing in established biofilm colonies. The material is typically initially stored within a container which may, or may not, be airtight, however, this step is one of practicality and is not deemed an important aspect of the present invention.

The second step requires providing packaging material having specific dimensional parameters such that marine material packaged therein preferably forms a uniform layer between ½-inch and 3-inches in depth. The 3-inch depth maximum limitation is considered important in that it allows both water and gas (contained in the packaging along with the harvested material as discussed below) to diffuse sufficiently through the material thereby providing vital, life sustaining nutrients to the bacteria at all depths. It should be noted, however, that packaging the harvested material in layers exceeding the preferred 3-inch maximum is not a departure from the present invention as bacteria existing in the region of the top 3-inches of deeper layers will remain capable of metabolic and physiologic activity as described herein.

The third step includes depositing the harvested marine material in the packaging material along with sea water and air in the following relative ratios: 1 lb. of harvested material (e.g. sand, aragonite etc.); 2–12 fluid oz. (preferably between 4–6 fluid oz.) of sea water; and 5–100 cm$^3$ (preferably between 10–50 cm$^3$) of air. The fifth step includes sealing the packaging in an airtight manner.

It has been found that the above-referenced ratios of: (1) harvested material (forming a layer of 3-inches or less); (2) sea water; and (3) air; packaged in a sealed container provides a unique life sustaining environment wherein natural marine bacteria are capable of surviving for extended periods in excess of twelve (12) months. The retail packaging material preferably comprises a suitable plastic (either hard or soft/flexible). The contents of the package may be stored at room temperature without adversely affecting the biological viability of the marine bacteria. After an extended shelf life of twelve (12) months at room temperature, the contents of the package may be introduced into an aquarium and contribute to rapid cycling to remove nitrogenous waste and maintaining and/or restoring a natural organic balance thereby resulting in a healthy aquarium habitat.

According to a second aspect of the present invention there is disclosed an enrichment solution for further increasing the number of microorganisms that remain bio-actively viable. The enrichment solution may be used in combination with the method of the first aspect of the invention to further enhance the number of microorganisms that remain bio-actively viable during periods of extended storage. Specifically, a second aspect of the invention includes enriching the seawater used to package harvested marine material, such as sand, aragonite and crushed coral. According to the present invention an enrichment solution may include one or more of the following substances: a buffer; vitamins; proteins and/or amino acids; sugars; trace elements (e.g. minerals); Sodium Nitrate (NaNO$_3$); Sodium Phosphate (NaH$_2$PO$_4$H$_2$O).

In a preferred embodiment according to the second aspect of the present invention a sea water enrichment solution is prepared in accordance with the formula described in FIG. 1, whereby the solutions of FIGS. 2, 3, and 4 are combined with a predetermined quantity of sea water (filtered and sterilized after all additions), with predetermined quantities of Sodium Nitrate and Sodium Phosphate.

It has been found that the critical level of moisture necessary to keep the bacteria viable but dormant for more than six months is from 2 to 12 oz. of fortified, sterile-filtered, sea water per pound of live marine sand. Preferably 4 to 8 oz. of fortified sterile seawater is used. Most preferably, the critical level of moisture is generated by the addition of 6 oz. of fortified sterile-filtered seawater per pound of live marine material (e.g. sand, aragonite etc.). The seawater may be fortified with sterile seawater enrichment solution (FIG. 1; one liter of seawater enrichment solution is added to 100 gallons of seawater) and maintained in a sterile state until used.

It has been found that marine aragonite sand subjected to the process disclosed herein is likely to contain not less than 10,000,000 live heterotrophic bacteria per pound. The process results in a natural product that prevents bio-fouling, and contains live marine autotrophic bacteria to provide a proper inorganic balance. The beneficial characteristics of the process using aragonite sand include: (1) reducing harmful nitrate; (2) maintaining proper pH; (3) providing enhanced buffering capacity; and (4) providing essential inorganic elements such as strontium, cobalt, zinc, and molybdenum. In addition, the following trace elements are provided: Zinc Sulfate; Calcium Chloride, Manganese Chloride; Cobalt Chloride; Copper Sulfate; Sodium Molybdate; Strontium Chloride; Nickel Chloride; Potassium Bromide; and Sodium Silicate.

Attached hereto as Appendix A and B are Applicants' findings, over time, with respect to the amount of live bacteria per gram of marine aragonite reef sand packaged in accordance with the present invention both with the seawater enrichment solution (Appendix A) and without (Appendix B).

The instant invention has been shown and described herein in what is considered to be the most practical and preferred embodiment. It is recognized, however, that departures may be made therefrom within the scope of the invention and that obvious modifications will occur to a person skilled in the art.

APPENDIX A

VIABLE BACTERIAL COUNTS FOR BIO-ACTIV LIVE ™ ARAGONITE
(Preserved with Saltwater Enrichment Solution)

| Media and Incubation Conditions | Dilution & Storage Conditions | Sample ID. | CFU/gm | Date Tested |
|---|---|---|---|---|
| Marine Agar: At Room Temp | 1:10 - Kept at Room Temp | Bag #3 A | 83,941 | 4/26/98 |
| Marine Agar: At Room Temp | 1:10 - Kept at Room Temp | Bag #3 A | 86,622 | 4/26/98 |
| Marine Agar: At Room Temp | 1:10 - Kept at Room Temp | Bag #3 B | 101,199 | 4/26/98 |
| Marine Agar: At Room Temp | 1:10 - Kept at Room Temp | Bag #3 B | 99,425 | 4/26/98 |
| | | Average | 92,797 | |
| Marine Agar: At Room Temp | 1:10 - Kept at Room Temp | Bag #7 A | 78,877 | 7/19/98 |
| Marine Agar: At Room Temp | 1:10 - Kept at Room Temp | Bag #7 A | 86,594 | 7/19/98 |
| Marine Agar: At Room Temp | 1:10 - Kept at Room Temp | Bag #7 B | 86,093 | 7/19/98 |
| Marine Agar: At Room Temp | 1:10 - Kept at Room Temp | Bag #7 B | 76,556 | 7/19/98 |
| | | Average | 82,030 | |
| Marine Agar: At Room Temp | 1:10 - Kept at Room Temp | Bag #10 A | 121,619 | 10/5/98 |
| Marine Agar: At Room Temp | 1:10 - Kept at Room Temp | Bag #10 A | 125,307 | 10/5/98 |
| Marine Agar: At Room Temp | 1:10 - Kept at Room Temp | Bag #10 B | 99,334 | 10/5/98 |
| Marine Agar: At Room Temp | 1:10 - Kept at Room Temp | Bag #10 B | 99,966 | 10/5/98 |
| | | Average | 111,557 | |
| Marine Agar: At Room Temp | 1:10 - Kept at Room Temp | Bag #12 A | 83,941 | 1/5/99 |
| Marine Agar: At Room Temp | 1:10 - Kept at Room Temp | Bag #12 A | 38,905 | 1/5/99 |
| Marine Agar: At Room Temp | 1:10 - Kept at Room Temp | Bag #12 B | 44,173 | 1/5/99 |
| Marine Agar: At Room Temp | 1:10 - Kept at Room Temp | Bag #12 B | 45,440 | 1/5/99 |
| | | Average | 53,115 | |

APPENDIX A-continued

VIABLE BACTERIAL COUNTS FOR BIO-ACTIV LIVE ™ ARAGONITE
(Preserved with Saltwater Enrichment Solution)

| Media and Incubation Conditions | Dilution & Storage Conditions | Sample ID. | CFU/gm | Date Tested |
|---|---|---|---|---|
| Marine Agar: At Room Temp | 1:10 - Kept at Room Temp | Bag #13 A | 37,756 | 5/1/99 |
| Marine Agar: At Room Temp | 1:10 - Kept at Room Temp | Bag #13 A | 46,084 | 5/1/99 |
| Marine Agar: At Room Temp | 1:10 - Kept at Room Temp | Bag #13 B | 50,780 | 5/1/99 |
| Marine Agar: At Room Temp | 1:10 - Kept at Room Temp | Bag #13 B | 49,289 | 5/1/99 |
| | | Average | 45,977 | |
| Marine Agar: At Room Temp | 1:10 - Kept at Room Temp | Bag #2 A | 127,471 | 4/26/98 |
| Marine Agar: At Room Temp | 1:10 - Kept at Room Temp | Bag #2 A | 122,142 | 4/26/98 |
| Marine Agar: At Room Temp | 1:10 - Kept at Room Temp | Bag #4 B | 169,778 | 4/26/98 |
| Marine Agar: At Room Temp | 1:10 - Kept at Room Temp | Bag #4 B | 153,889 | 4/26/98 |
| | | Average | 143,320 | |
| Marine Agar: At Room Temp | 1:10 - Kept at Room Temp | Bag #5 A | 50,051 | 6/19/98 |
| Marine Agar: At Room Temp | 1:10 - Kept at Room Temp | Bag #5 A | 45,304 | 6/19/98 |
| Marine Agar: At Room Temp | 1:10 - Kept at Room Temp | Bag #8 B | 21,540 | 6/19/98 |
| Marine Agar: At Room Temp | 1:10 - Kept at Room Temp | Bag #8 B | 23,510 | 6/19/98 |
| | | Average | 35,101 | |
| Marine Agar: At Room Temp | 1:10 - Kept at Room Temp | Bag #11 A | 32,017 | 9/5/98 |
| Marine Agar: At Room Temp | 1:10 - Kept at Room Temp | Bag #11 A | 27,332 | 9/5/98 |
| Marine Agar: At Room Temp | 1:10 - Kept at Room Temp | Bag #11 B | 24,928 | 9/5/98 |
| Marine Agar: At Room Temp | 1:10 - Kept at Room Temp | Bag #11 B | 24,123 | 9/5/98 |
| | | Average | 27,100 | |
| Marine Agar: At Room Temp | 1:10 - Kept at Room Temp | Bag #12 A | 16,010 | 11/5/99 |
| Marine Agar: At Room Temp | 1:10 - Kept at Room Temp | Bag #12 A | 19,913 | 11/5/99 |
| Marine Agar: At Room Temp | 1:10 - Kept at Room Temp | Bag #12 B | 24,123 | 11/5/99 |
| Marine Agar: At Room Temp | 1:10 - Kept at Room Temp | Bag #12 B | 32,017 | 11/5/99 |
| | | Average | 23,016 | |
| Marine Agar: At Room Temp | 1:10 - Kept at Room Temp | Bag #1 A | 10,125 | 4/22/99 |
| Marine Agar: At Room Temp | 1:10 - Kept at Room Temp | Bag #1 A | 10,613 | 4/22/99 |
| Marine Agar: At Room Temp | 1:10 - Kept at Room Temp | Bag #1 B | 12,924 | 4/22/99 |
| Marine Agar: At Room Temp | 1:10 - Kept at Room Temp | Bag #1 B | 12,160 | 4/22/99 |
| | | Average | 11,456 | |

What is claimed is:

1. A method for preserving natural marine bacteria embodied in a biofilm attached to sand particles in sealed retail packaging containing a seawater enrichment solution such that the bacteria remains capable of metabolic and physiologic activity after prolonged periods exceeding one year without the intermittent addition of air, water, or food, said method comprising:

harvesting sand from a natural submerged marine environment;

depositing said harvested sand in packaging with between 2 and 12 fluid ounces of the seawater enrichment solution and between 5 cm³ and 100 cm³ of air for every 1 pound of sand, wherein the seawater enrichment solution comprises sodium nitrate, sodium dihydrogen phosphate, vitamins, organic stock solution, trace metals and seawater; and sealing said packaging in an airtight manner.

2. A method of preserving marine bacteria according to claim 1, wherein said amount of the seawater enrichment solution is between 4 and 6 fluid ounces for every 1 pound of sand.

3. A method of preserving marine bacteria according to claim 1, wherein said amount of air is between 10 and 50 cm³ for every 1 pound of sand.

4. A method of preserving marine bacteria according to claim 1, wherein said organic stock solution contains proteins.

5. A method of preserving natural marine bacteria embodied in biofilm attached to sand particles in sealed retail packaging containing a seawater enrichment solution such that the bacteria remains capable of metabolic and physiologic activity after prolonged periods exceeding one year without the intermittent addition of air, water, or food, said method comprising:

harvesting marine sand from a natural submerged marine environment;

preventing said marine sand from drying;

depositing said harvested marine sand in packaging, such that said sand forms a generally uniform layer having a maximum depth of 3 inches;

adding between 2 and 12 fluid ounces of the seawater enrichment solution in said packaging for every 1 pound of sand, wherein the seawater enrichment solution comprises sodium nitrate, sodium dihydrogen phosphate, vitamins, organic stock solution, trace metals and seawater;

adding between 5 and 100 cm³ of air in said packaging for every 1 pound of sand;

sealing said packaging in an airtight manner.

\* \* \* \* \*

UNITED STATES PATENT AND TRADEMARK OFFICE
CERTIFICATE OF CORRECTION

| | |
|---|---|
| PATENT NO. | : 6,376,229 B2 |
| DATED | : April 23, 2002 |
| INVENTOR(S) | : Barrington A. Morris and Eric A. Goulbourne, Jr. |

It is certified that error appears in the above-identified patent and that said Letters Patent is hereby corrected as shown below:

<u>Columns 9 & 10,</u>
In the Appendix A, a table heading should be inserted below the statistics for bags 13A and 13B tested 5/1/99 and above the statistics for bags 2A and 4B tested 4/26/98 that reads as follows:

```
                            Appendix B
─────────────────────────────────────────────────────────────────
  Viable bacterial counts for bio-activ live aragonite
  (without saltwater enrichment solution)
─────────────────────────────────────────────────────────────────
   Media and Incubation Conditions  Dilution & Storage Conditions Sample ID.   CFU/gm  Date Tested
```

Signed and Sealed this

Sixteenth Day of December, 2003

JAMES E. ROGAN
*Director of the United States Patent and Trademark Office*